United States Patent
Reichow et al.

(10) Patent No.: US 10,226,171 B2
(45) Date of Patent: Mar. 12, 2019

(54) VISION COGNITION AND COORDINATION TESTING AND TRAINING

(75) Inventors: Alan W. Reichow, Beaverton, OR (US); Ryan C. Coulter, Portland, OR (US); Herb Yoo, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 1022 days.

(21) Appl. No.: 12/595,210

(22) PCT Filed: Apr. 14, 2008

(86) PCT No.: PCT/US2008/060252
§ 371 (c)(1),
(2), (4) Date: Mar. 24, 2010

(87) PCT Pub. No.: WO2008/128192
PCT Pub. Date: Oct. 23, 2008

(65) Prior Publication Data
US 2010/0216104 A1    Aug. 26, 2010

Related U.S. Application Data (60) Provisional application No. 60/941,915, filed on Jun. 4, 2007, provisional application No. 60/923,434, filed on Apr. 13, 2007.

(51) Int. Cl.
*A61B 3/032* (2006.01)
*A61B 5/00* (2006.01)
(Continued)

(52) U.S. Cl.
CPC .............. *A61B 3/032* (2013.01); *A61B 5/16* (2013.01); *A61B 5/7475* (2013.01); *G09B 17/02* (2013.01);
(Continued)

(58) Field of Classification Search
CPC .......... A61B 5/16; A61B 5/162; A61B 3/032; A61B 3/02; A61B 3/028; A61B 5/04842;
(Continued)

(56) References Cited

U.S. PATENT DOCUMENTS

| | | |
|---|---|---|
| 3,861,790 A | 1/1975 | Tamura |
| 4,528,989 A | 7/1985 | Weinblatt |

(Continued)

FOREIGN PATENT DOCUMENTS

| | | |
|---|---|---|
| EP | 1297865 A1 | 4/2003 |
| JP | H024309 A | 1/1990 |

(Continued)

OTHER PUBLICATIONS

Office Action dated Apr. 6, 2011 in U.S. Appl. No. 12/595,209, 16 pages.

(Continued)

*Primary Examiner* — Jack Yip
(74) *Attorney, Agent, or Firm* — Shook, Hardy & Bacon L.L.P.

(57) ABSTRACT

The visual, cognitive, and coordination skills of a subject may be tested and/or trained by providing a variety of stimuli to a subject. Responses may be received from a subject, the appropriateness of which may depend upon the combination of stimuli provided to the subject. A touch screen display device may be used both to provide stimuli and to receive responses from a subject. Any number and type of output devices and input devices to receive responses may be used. Behavioral information and other data regarding the performance of a subject may be recorded. Scoring may be based upon the speed, accuracy, and other aspects of the performance of a subject.

20 Claims, 7 Drawing Sheets

(51) Int. Cl.
| | |
|---|---|
| G09B 17/02 | (2006.01) |
| G09B 19/00 | (2006.01) |
| A61B 3/02 | (2006.01) |
| A61B 5/0484 | (2006.01) |
| A61H 5/00 | (2006.01) |
| A61B 5/16 | (2006.01) |
| A61B 5/103 | (2006.01) |

(52) U.S. Cl.
CPC ............ *G09B 19/0038* (2013.01); *A61B 3/02* (2013.01); *A61B 5/04842* (2013.01); *A61B 5/1036* (2013.01); *A61B 5/162* (2013.01); *A61H 5/00* (2013.01)

(58) Field of Classification Search
CPC ...... A61B 5/7475; A61B 5/1036; A61H 5/00; G09B 17/02; G09B 19/0038
USPC ................ 434/350, 236; 351/161; 73/379.01
See application file for complete search history.

(56) References Cited

U.S. PATENT DOCUMENTS

| | | | |
|---|---|---|---|
| 4,869,589 A | 9/1989 | Blair et al. | |
| 5,050,982 A | 9/1991 | Meissner | |
| 5,088,810 A | 2/1992 | Galanter | |
| 5,478,239 A | 12/1995 | Fuerst | |
| 5,520,393 A * | 5/1996 | Rickey, Jr. | 273/237 |
| 5,812,239 A | 9/1998 | Eger | |
| 5,825,460 A | 10/1998 | Kohayakawa | |
| 5,919,149 A | 7/1999 | Allum | |
| 6,067,986 A * | 5/2000 | Kluger | A61B 5/1036 600/595 |
| 6,092,058 A | 7/2000 | Smyth | |
| 6,206,702 B1 * | 3/2001 | Hayden | A61B 5/4076 434/236 |
| 6,261,239 B1 | 7/2001 | Abraham-fuchs | |
| 6,267,733 B1 | 7/2001 | Peterson et al. | |
| 6,364,845 B1 | 4/2002 | Duffy et al. | |
| 6,371,931 B1 | 4/2002 | Guillen | |
| 6,386,706 B1 * | 5/2002 | McClure | A61B 3/024 351/237 |
| 6,430,997 B1 * | 8/2002 | French et al. | 73/379.04 |
| 6,632,174 B1 | 10/2003 | Breznitz | |
| 6,755,525 B2 | 6/2004 | Reichow | |
| 6,796,927 B2 | 9/2004 | Toyama | |
| 6,811,258 B1 | 11/2004 | Grant | |
| 6,893,127 B2 | 5/2005 | Reichow | |
| 7,073,208 B2 | 7/2006 | Penque | |
| 7,326,060 B2 | 2/2008 | Seiller et al. | |
| 7,849,115 B2 | 12/2010 | Reiner | |
| 8,240,851 B2 | 8/2012 | Reichow et al. | |
| 8,513,055 B2 | 8/2013 | Reichow et al. | |
| 2002/0188219 A1 | 12/2002 | Suchard | |
| 2003/0048280 A1 * | 3/2003 | Russell | G06F 3/017 345/619 |
| 2003/0120183 A1 | 6/2003 | Simmons | |
| 2003/0211449 A1 | 11/2003 | Seiller et al. | |
| 2004/0141152 A1 | 7/2004 | Marino et al. | |
| 2004/0167380 A1 * | 8/2004 | Simon | 600/300 |
| 2005/0053904 A1 | 3/2005 | Shephard | |
| 2005/0273017 A1 | 12/2005 | Gordon | |
| 2006/0161218 A1 | 7/2006 | Danilov | |
| 2006/0194178 A1 | 8/2006 | Goldstein | |
| 2006/0195018 A1 | 8/2006 | Guillen | |
| 2006/0244915 A1 | 11/2006 | Clemons et al. | |
| 2006/0251334 A1 | 11/2006 | Oba et al. | |
| 2006/0281061 A1 | 12/2006 | Hightower et al. | |
| 2006/0287617 A1 | 12/2006 | Taub | |
| 2007/0000007 A1 | 1/2007 | MacDonald | |
| 2007/0013870 A1 | 1/2007 | Hara | |
| 2007/0027369 A1 | 2/2007 | Pagnacco et al. | |
| 2007/0052674 A1 | 3/2007 | Culver | |
| 2007/0179534 A1 | 8/2007 | Firlik et al. | |
| 2007/0184953 A1 | 8/2007 | Luberski et al. | |
| 2007/0197938 A1 * | 8/2007 | Tyson | A61B 5/1072 600/587 |
| 2007/0254270 A1 | 11/2007 | Hersh | |
| 2008/0003553 A1 | 1/2008 | Stark et al. | |
| 2008/0189173 A1 | 8/2008 | Bakar et al. | |
| 2008/0191864 A1 * | 8/2008 | Wolfson | G06F 3/011 340/524 |
| 2009/0093305 A1 | 4/2009 | Okamoto et al. | |
| 2009/0129205 A1 | 5/2009 | Reichow | |
| 2009/0130640 A1 | 5/2009 | Hardy | |
| 2009/0150919 A1 | 6/2009 | Lee | |

FOREIGN PATENT DOCUMENTS

| | | |
|---|---|---|
| JP | 06165755 A | 6/1994 |
| JP | 6217938 | 8/1994 |
| JP | 6237895 | 8/1994 |
| JP | H-07-005679 | 1/1995 |
| JP | 7299033 | 11/1995 |
| JP | 10305016 | 11/1998 |
| JP | H 11225961 | 2/1999 |
| JP | 11267101 | 10/1999 |
| JP | 11318824 | 11/1999 |
| JP | 2002219117 A | 8/2002 |
| JP | 2003102868 | 4/2003 |
| JP | 2003126036 | 5/2003 |
| JP | 2004135756 | 5/2004 |
| JP | 2004329795 A | 11/2004 |
| WO | 9802083 A2 | 1/1998 |
| WO | 2000128192 | 3/2000 |
| WO | 2002102469 | 12/2002 |
| WO | 2004006747 | 1/2004 |
| WO | 2006029048 | 3/2006 |
| WO | 2006088415 | 8/2006 |
| WO | 2007009990 A1 | 1/2007 |
| WO | 2008128183 A1 | 10/2008 |
| WO | 2008128192 | 10/2008 |

OTHER PUBLICATIONS

Office Action dated Jan. 6, 2011 in U.S. Appl. No. 12/117,315, 16 pages.
Final Office Action dated May 26, 2011 in U.S. Appl. No. 12/117,315, 10 pages.
Final Office Action in U.S. Appl. No. 12/500,385 dated Nov. 6, 2012, 43 pages.
Office Action in U.S. Appl. No. 12/595,208 dated Nov. 28, 2011, 20 pages.
EP Office Action Application No. 08 780 526.3-2319 dated Nov. 28, 2012.
A. Ludeke, et al., "The difference in visual skills between professional versus non-professional rugby players" The South African Optometrist, Dec. 1, 2003 pp. 150-158, XP055044423.
Martjin LTM Muller:"Attentional components of postural control" Dissertation, 2007, XP055044427, Saline MI (USA) Retrieved from the Internet: URL: http://dare.uva.n./document/48212 [retrieved on Nov. 15, 2012].
Non-Final Office Action in U.S. Appl. No. 13/584,454 dated Apr. 11, 2013, 35 pages.
Notice of Allowance in U.S. Appl. No. 12/595,209, dated Apr. 10, 2013, 31 pages.
Notice of Allowance and Fees Due in U.S. Appl. No. 12/595,207 dated Apr. 12, 2012, 79 pages.
Non-Final Office Action in U.S. Appl. No. 12/595,209 dated Jul. 13, 2012, 32 pages.
Final Office Action in U.S. Appl. No. 12/595,208 dated May 10, 2012, 25 pages.
Final Office Action in U.S. Appl. No. 12/595,209 dated Jan. 13, 2012, 17 pages.
Non-Final Office Action in U.S. Appl. No. 12/500,385 dated Mar. 19, 2012, 39 pages.
Cardall, "Contact Lenses in Sport: a General Overview", Optician, Jan. 13, 2006, pp. 22-25, vol. 231, No. 6034, United States.

(56) References Cited

OTHER PUBLICATIONS

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.
Office Action dated Jul. 12, 2011 in U.S. Appl. No. 12/595,209.
International Search Report and Written Opinion for PCT/US2010/041564, dated Nov. 12, 2010.
International Search Report and Written Opinion for PCT/US08/60229, dated Sep. 9, 2008, 9 pages.
Supplementary European Search Report for EP08745763, Completed Jun. 16, 2010, 9 Pages.
Rouse, et al., "A Comparison Study of Dynamic Visual Acuity Between Athletes and Nonathletes", Journal of the American Optometric Association, Dec. 1988, pp. 946-950, vol. 59, No. 12, United States.
Coffey, et al, "Optometric Evaluation of the Elite Athlete," Problems in Optometry, Mar. 1990, pp. 32-59, vol. 2, No. 1, United States.
Reichow, et al., "Introduction to Behavioral Optometry", Sports Vision, 1993, 75 pages, Optometric Extension Program Foundation, United States.
Reichow, et al., "A Comparison of Contrast Sensitivity in Elite Athletes Versus a Normal Population", American Journal of Optometry and Physiological Optics, Dec. 15, 1986, vol. 63, No. 82, United States.
Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.
Herdman, et al., "Computerized Dynamic Visual Acuity Test in the Assessment of Vestibular Deficits", The American Journal of Otology, 1998, pp. 790-796, vol. 19, No. 6, United States.
Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.
"Coffey, et al., "Visual Performance Enhancement in Sports Optometry"", Sports Vision 1995, pp. 158-177, Butterworth-Heinermann, United States.
Ferreira, "An Overview of Research in Sports Vision: its History and an Optometric Perspective", The South African Optometrist, Dec. 2003, pp. 142-149, vol. 62, No. 4, Auckland Park, South Africa.
Koenig, "Practicing Perception: Eyes Can Be Trained to be More Effective", USA Today Baseball Weekly, 1996, 3 pages, United States.
International Search Report and Written Opinion for PCT/US08/60249, dated Sep. 8, 2008, 9 Pages.
Supplementary European Search Report for EP08745783, Completed Jun. 23, 2010, 10 Pages.
International Search Report and Written Opinion for PCT/US08/60244, dated Sep. 4, 2008, 9 Pages.
Supplementary European Search Report for EP08745778.4, Completed Jun. 23, 2010, 9 Pages.
Supplementary European Search Report for EP08780526, Completed Jun. 16, 2010, 11 Pages.
International Search Report and Written Opinion for PCT/US08/60252, dated Aug. 15, 2008, 10 Pages.
International Search Report and Written Opinion for PCT/US09/043127, dated Jul. 6, 2009, 11 Pages.
Office Action in U.S. Appl. No. 12/595,207 dated Nov. 10, 2011, 19 pages.
Final Office Action in U.S. Appl. No. 13/584,454, dated Dec. 24, 2013, 25 pages.
Official Guidebook by Nintendo, "Rhythm Heaven", Shogajujan, Inc., Nov. 1, 2006, pp. 4, 5, 14, 15, 26, 27, 28, 29.
Kazutaka Toyoomi, Nintendo has improved "Visual Ability" through a simple training. DS software: "DS Visual Ability Training for Improving Ability to See through Actual Practice" Game Watch, May 18, 2007, http://game.watch.impress.co.jp/docs/20070518/meji.htm.
Shigenori Agura, "Sports Vision", Science for Children, October issue, Sep. 17, 2002, vol. 65 (10), pp. 10-18.
Canadian Office Action dated Jan. 28, 2015 in Canadian Patent Application No. 2,683,728, 3 pages.
Canadian Office Action dated Jan. 28, 2015 in Canadian Patent Application No. 2,683,808, 3 pages.
Notice of Allowance dated Feb. 11, 2015 in U.S. Appl. No. 12/500,385, 11 pages.
European Search Report dated Mar. 19, 2015 in European Patent Application No. 09743649.7, 7 pages.
Final Office Action dated May 18, 2015 in U.S. Appl. No. 12/117,315, 9 pages.
European Office Action dated Jun. 24, 2015 in European Patent Application No. 10797929.6, 5 pages.
Canadian Office Action dated Sep. 2, 2015 in Canadian Patent Application No. 2,725,211, 5 pages.
Canadian Office Action dated Nov. 24, 2015 in Canadian Patent Application No. 2,767,654, 5 pages.
European Office Action dated Apr. 26, 2016 in European Patent Application No. 08745783.4, 6 pages.
European Office Action dated Apr. 26, 2016 in European Patent Application No. 08745778.4, 6 pages.
Non-Final Office Action dated Jun. 1, 2016 in U.S. Appl. No. 12/117,315, 14 pages.
Kathryn W. O'Connor et al.: "Postural adaptations to repeated optic flow stimulation in older adults", Gait & Posture, vol. 28, No. 3, Mar. 10, 2008, pp. 385-391. Retrieved from the Internet Sep. 9, 2014: URL:http://www.ncbi.nlm.nih.gov/pmc/articles/PMC2605319/.
Mark S Redfern et al.: "Attention influences sensory integration for postural control in older adults", Gait & Posture, vol. 14, No. 3, Dec. 1, 2001, pp. 211-216.
European Search Report dated Sep. 26, 2014 in Application No. 10797929.6, 13 pages.
Notice of Allowance dated Apr. 7, 2014 in U.S. Appl. No. 13/584,454, 7 pages.
Non-Final Office Action dated Oct. 31, 2004 in U.S. Appl. No. 12/117,315, 9 pages.
European Office Action dated Jun. 27, 2016, in European Patent Application No. 09743649.7, 8 pages.
European Office Action dated Jul. 6, 2016, in European Patent Application No. 09780526.3, 6 pages.
Canadian Office Action dated Jul. 15, 2016, in Canadian Patent Application No. 2725211, 6 pages.
European Notice of Allowance dated Jul. 19, 2016, in European Patent Application No. 08745763.6, 27 pages.
U.S. Notice of Allowance dated Sep. 22, 2016, in U.S. Appl. No. 12/117,315, 40 pages.
European Notice of Allowance dated Jan. 24, 2017 in European Patent Application No. 08780526.3, 31 pages.
Canadian Office Action dated Mar. 10, 2017 in Canadian Patent Application No. 2767654, 6 pages.
Office Action dated Sep. 1, 2017 in European Patent Application No. 09743649.7, 5 pages.
Non-Final Office Action dated Feb. 26, 2018 in U.S. Appl. No. 15/389,516, 10 pages.
Canadian Examiner's Report dated Jun. 29, 2017 in Canadian Patent Application No. 2,725,211, 6 pages.

* cited by examiner

VISION COGNITION AND COORDINATION TESTING AND TRAINING

CROSS-REFERENCE TO RELATED APPLICATIONS

This application claims priority to U.S. Provisional Application No. 60/923,434 filed on Apr. 13, 2007, entitled "System and Method for Testing Visual Ability During Simulated Activity," which is hereby incorporated by reference. This application also claims priority to U.S. Provisional Application No. 60/941,915 filed on Jun. 4, 2007, entitled "System and Method for Decoupled Visual Ability Testing," which is hereby incorporated by reference.

STATEMENT REGARDING FEDERALLY SPONSORED RESEARCH OR DEVELOPMENT

Not applicable.

TECHNICAL FIELD

The present invention relates generally to the testing and training of vision, cognitive function, and coordination. More particularly, the present invention relates to training and testing eye-hand coordination and/or cognitive processing and response to various stimuli.

BACKGROUND OF THE INVENTION

One skilled in the art of vision evaluation will be aware of a large number of vision tests that may be performed upon a subject to determine the strengths and weaknesses of an individual's visual abilities. Typically, such tests are applied to determine whether an individual may benefit from some form of vision correction and/or training and, if so what type and degree of vision correction and/or training may be desirable. One skilled in the art will further realize that numerous activities, particularly competitive athletics, place particularized demands upon the visual abilities of an individual.

SUMMARY OF THE INVENTION

Systems and methods in accordance with the present invention test the vision and/or cognition abilities of a subject by providing a variety of stimuli and receiving responses from a subject. Stimuli presented to a subject may be, for example, visual stimuli presented on a display device. One example of an appropriate display device is a touch-sensitive display device, such as a touch screen. Such a touch screen may function as both a display device and an input device. A touch screen device may be particularly useful for testing eye-hand coordination, sometimes also referred to as hand-eye coordination. By using a touch screen for both display and input purposes, systems and methods in accordance with the present invention may accurately measure both the speed and/or accuracy of a subject's touch response to visual stimuli.

Systems and methods in accordance with the present invention may further test or train a subject's ability to respond to multiple stimuli, particularly when a subject must perform cognitive processing to make a response or to determine an appropriate response. For example, a response to a first visual stimuli may be appropriate only when the visual stimuli is paired with a second stimuli. A second stimuli may be, for example, a particular sound, a particular additional visual indicia, a particular tactile sensation, or any other type of stimuli. The second stimuli may also be a particular trait possessed by the first stimuli, such as a directional orientation, a location upon a display device, a color, etc. Some or all of the stimuli used in systems and methods in accordance with the present invention may require cognitive processing by subject. For example, a series of digits may have to be read by a subject, or a subject must perceive the directional orientation of a displayed indicia, or any of a number of other determinations or tasks may be required of a subject as part of the subject's response.

Systems and methods in accordance with the present invention may further record additional data regarding a subject's performance beyond metrics such as accuracy and speed of performance. For example, data regarding a subject's balance, eye movements, head movements, other movements, or medical/biological data may be recorded as part of testing and/or training.

Systems and methods in accordance with the present invention may utilize a variety of display devices and display techniques. While a touch-sensitive display device is one example of an appropriate display in accordance with the present invention, any display device, including monitors, projection screens, projection goggles, holograms, or other display devices may be used. The type of visual stimuli presented using a display may also vary. For example, a display may simply provide the stimuli used for testing/training alone, or presented stimuli may be integrated into a video simulation of an activity. For example, testing/training designed to improve a baseball player's hitting ability could depict a video representation of a pitcher releasing a ball toward the plate. A variety of display devices, such as arcuate screens, partially spherical screens, multiple screens, and/or display goggles may be useful to provide a more immersive experience to a subject and/or to test/train a subject in a variety of visual fields.

BRIEF DESCRIPTION OF THE DRAWING

The present invention is described in detail below with reference to the attached drawing figures, wherein.

DETAILED DESCRIPTION OF THE INVENTION

Figure 1:
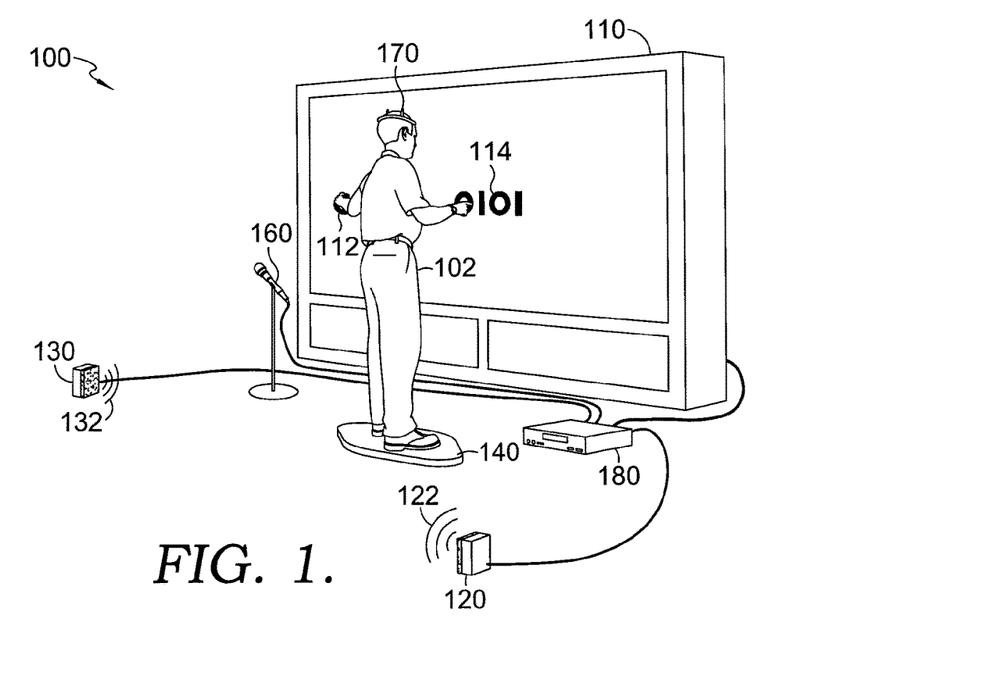
FIG. 1 illustrates a system in accordance with the present invention.

Referring now to the figures, FIG. 1 illustrates a testing/training system 100 in accordance with the present invention. It will be understood by one of ordinary skill in the art that the systems and methods described herein may be applicable for both testing and training purposes. System 100 may be used to test/train subject 102. Display device 110 may be positioned so that subject 102 may view display device 110. While a single display device 110 is illustrated in FIG. 1, multiple display devices may be used. Display device 110 may further be touch-sensitive, thereby permitting it to receive inputs as well. If display device 110 is touch-sensitive, it may be oriented within reach of subject 102 to permit display device 110 to receive touch inputs from subject 102. A touch-sensitive display device 110 may receive more than one touch input at a time. A touch-sensitive display device may comprise a monitor, projection screen, or any other type of display device without touch-sensitivity operatively coupled to a touch sensitive layer that permits both the display of visual stimuli and the receipt of touch inputs. For example, a touch-sensitive and substantially transparent film may be applied over a non-touch-sensitive monitor. By way of further example, a touch-sensitive board may be used in conjunction with a projector as a touch-sensitive display device 110. These and other possibilities for use as a touch-sensitive display device will be understood to those of ordinary skill in the art. Display device 110 may provide stimuli, such as first visual indicia 112 and second visual indicia 114. As illustrated in FIG. 1, first indicia 112 depicts one example of an appropriate indicia for use in the present invention, a Landolt C. A Landolt C is a visually neutral character that may possess an orientation of left, right, up, or down. However, one of ordinary skill in the art will appreciate that any other type of indicia may be used in accordance with the present invention. Second indicia 114 provides an additional example of an indicia that may be used in accordance with the present invention. As illustrated in FIG. 1, second indicia 114 is a short string of digits.

Still referring to FIG. 1, system 100 may include a first audio speaker 120 that may emit a first sound 122 and a second audio speaker 130 that may emit a second sound 132. Audio stimuli may be used in accordance with the present invention. For example, systems and methods in accordance with the present invention may use sound in conjunction with vision and/or cognition testing/training as part of preparing a subject to perform in a competitive environment where there may be distractions due to crowd noise or other sounds. Further, sound may be used as a stimuli requiring a particular response from a subject. Potentially, a subject may be required to respond in a given way to a particular combination of stimuli, such as responding to a visual stimuli only when paired with a particular sound. The use of multiple speakers 120, 130, even beyond the two depicted in FIG. 1, permits a subject to test/train to differentiate sounds based upon their direction of origin. Sound may also be used in accordance with the present invention for pace setting purposes, such as has been provided by metronomes.

Still referring to FIG. 1, a stability platform 140 may be placed beneath subject 102. Stability platform 140 may serve to provide further stimuli to subject 102 by, for example, providing tactile feedback to subject 102 by tilting in a variety of directions. Stability platform 140 may also be used to receive input responses from, subject 102, for example if subject 102 is to lean in a given direction in response to a given stimuli. Stability platform 140 also may record data regarding the balance and orientation of subject 102 during testing/training, either in addition to or instead of providing stimuli to a subject. Stability platform 140 may be any device that provides stability related stimuli to a subject and/or receives stability related inputs from a subject. For example, stability platform 140 may utilize one or more plates and sensors to detect shifts in the weight of a test subject. Stability platform 140 may, by way of further example, comprise a balance board that may tip around a fulcrum point. One skilled in the art will appreciate that any type of device that can provide stability related stimuli and/or stability related input may be used as stability platform 140.

Still referring to FIG. 1, a microphone 160 may also receive responses from subject 102. Microphone 160 may, for example, be used in conjunction with voice recognition software to receive vocal responses from subject 102. Examples of vocal responses include the identity of a series of digits displayed on display device 110, the orientation of an indicia displayed on display device 110, the color of an indicia displayed on display device 110, the region of display device 110 on which an indicia is displayed, or any other type of verbal information.

Further referring to FIG. 1, system 100 may include head and/or eye monitor 170. Head and/or eye monitor 170 may measure the movement of the head and/or eyes of subject 102 during testing/training. Other equipment (not illustrated) may measure data such as a subject's brain activity, blood pressure, heart rate, perspiration, or other biological and/or medical data. By way of example, without limitation, the brain activity of a subject may be used as an input device by utilizing an EEG to capture brain activity, particularly brain activity that is linked to the subject's vision.

Test unit 180 may coordinate the stimuli provided by various output devices in system 100 and collect and retain data from the responses of subject 102 and any additional data, such as balance, eye movement, head movement data, and biological/medical data received from subject 102. Test unit 180 may further provide scoring functionality to provide a measure of the accuracy, speed, and other performance criteria of subject 102. Test unit 180 may further control the testing process so that the presentation of stimuli to subject 102 increases in speed or difficulty as subject 102 progresses through testing/training.

Subject 102 may further provide responses using a motor input device (not shown). Motor input device may be any device, such as a joy stick or keypad, capable of receiving manual input from subject 102, and may also be any device capable of receiving input from any other type of physical action by subject 102, such as foot actuated pedals or buttons. Examples of appropriate devices for use as input device 150 include keyboards or keypads, buttons, joy sticks, switches, pedals, or any other device capable of receiving an active input from subject 102. One or more motor input device may be used in addition to or in place of a display device 110 with touch-sensitive properties.

Figure 2:
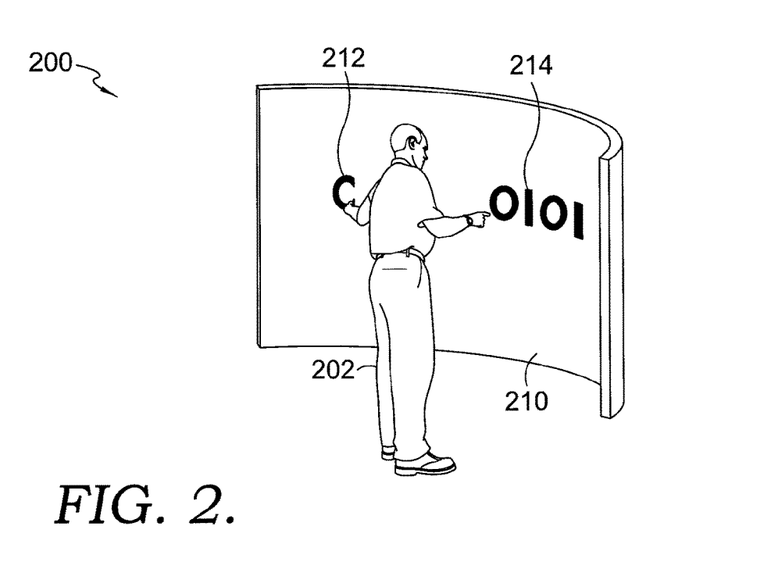
FIG. 2 illustrates a further system in accordance with the present invention.

Referring now to FIG. 2, a portion of a second example system 200 in accordance with the present invention is illustrated. System 200 utilizes an arcuate display device 210 oriented partially around subject 202. Arcuate display device 210 may display a first indicia 212 and a second indicia 214. System 200 may further include a variety of additional components, such as those illustrated in FIG. 1. Arcuate display device 210 may be useful to both provide subject 202 a more immersive visual experience, to test portions of the field of vision of subject 202 not easily tested/trained using a single flat display device, and to provide a more consistent hand-to-touch screen distance around the full field, thereby reducing motor variability that can confound testing and/or training results.

Figure 3:
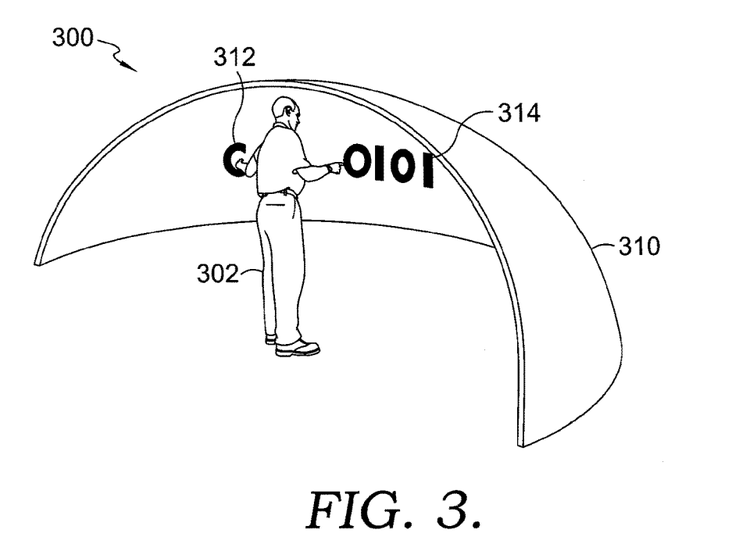
FIG. 3 illustrates a further system in accordance with the present invention.

Referring now to FIG. 3, yet a further portion of a system 300 in accordance with the present invention is illustrated. System 300 utilizes a portion of a spherical display device 310 that partially encloses subject 302. Partially spherical display device 310 may display thereon a first indicia 312 and a second indicia 314. System 300 may further include a variety of additional devices, such as those illustrated and described above with regard to FIG. 1. A partially spherical display device 310 may be useful both in providing a more immersive testing/training experience for subject 302, to test portions of the field of vision of subject 302 that could be difficult to test using a single flat display device, and to provide a more consistent hand-to-touch screen distance around the full field, thereby reducing motor variability that can confound testing and/or training results.

Figure 4:
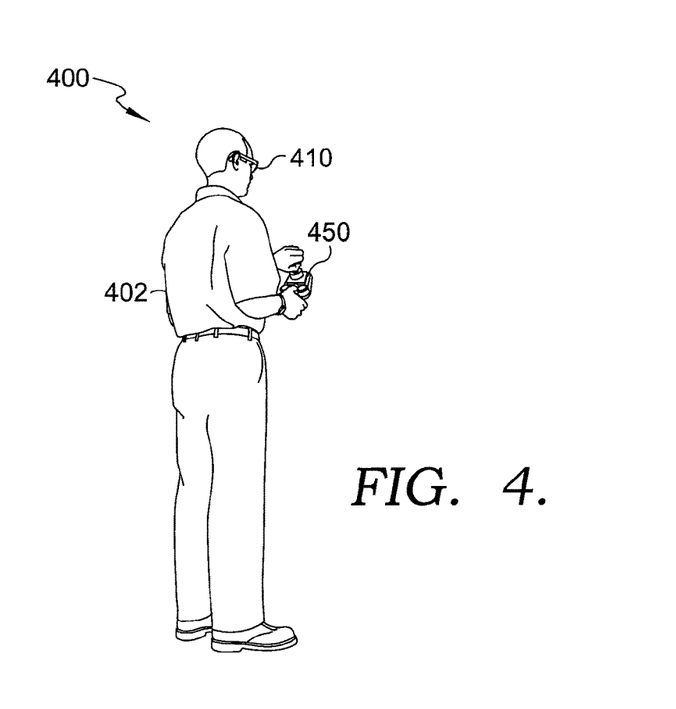
FIG. 4 illustrates a further system in accordance with the present invention.

Referring now to FIG. 4, a portion of a system 400 utilizing display goggles 410 are illustrated. Display goggles 410 may present visual imagery to subject 402 without the need for a larger display device. System 400 may include an input device 450 that may receive responses from subject 402. Input device 450 may be any of the input devices described above with regard to input device 150 in FIG. 1, or may alternatively be a microphone or balance board. Input device 450 may be, for example, a motion sensitive glove or other device worn by subject 402 to measure the movement of the hand of subject 402 in response to visual stimuli displayed using goggles 410 to measure the eye-hand coordination of subject 402. It should further be appreciated that goggles 410 may include integrally therein head and/or eye movement monitors, or other biological/medical monitors.

Figure 5:
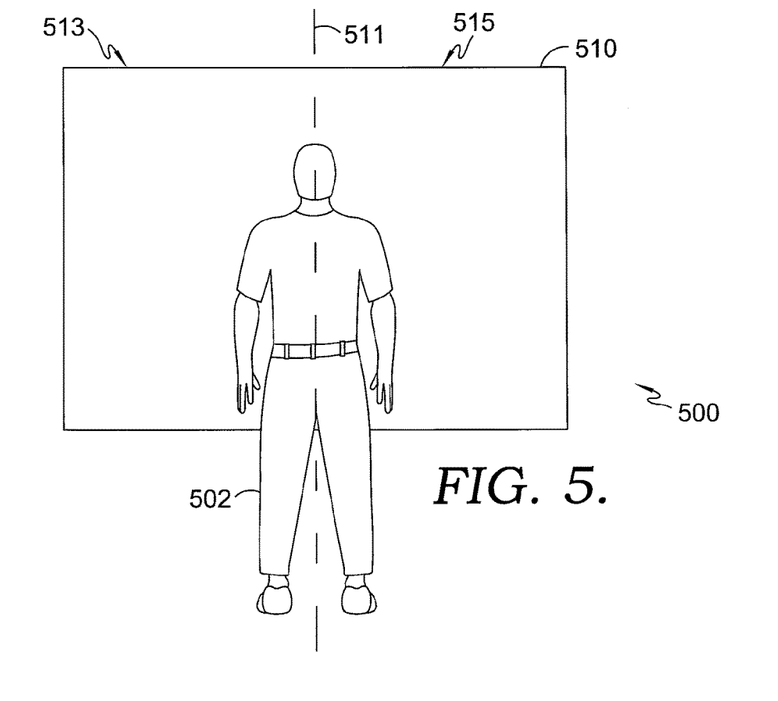
FIG. 5 illustrates the use of a display device in accordance with the present invention to isolate a single eye of a subject.

Referring now to FIG. 5, a portion of a system 500 is illustrated for testing/training the use of individual eyes by subject 502. Display device 510 is divided at midline 511 into a left section 513 and a right section 515 such that visual stimuli may be provided that are perceivable only through either the left or right eye of subject 502. The division of a display device 510 at midline 511 may be accomplished in any way. For example, display device 510 may comprise goggles or any other wavelength filtering optical device, in which case a given visual stimuli may be displayed on only one side of the goggles. Alternatively, a display device 510 such as a monitor may be utilized with a screen in place to limit the field of vision of each eye of subject 502 to only a portion of the display device 510, such that the eye used to perceive a displayed indicia is determined by the indicia's location on display device 510. Other techniques, such as the use of wavelength filtering goggles and appropriately colored indicia displayed on display device 510 may also isolate either the left or right eye of subject 502, although in such an instance a physical divider at midline 511 would no longer be needed to isolate the left and right eyes of subject 502.

Figure 6:
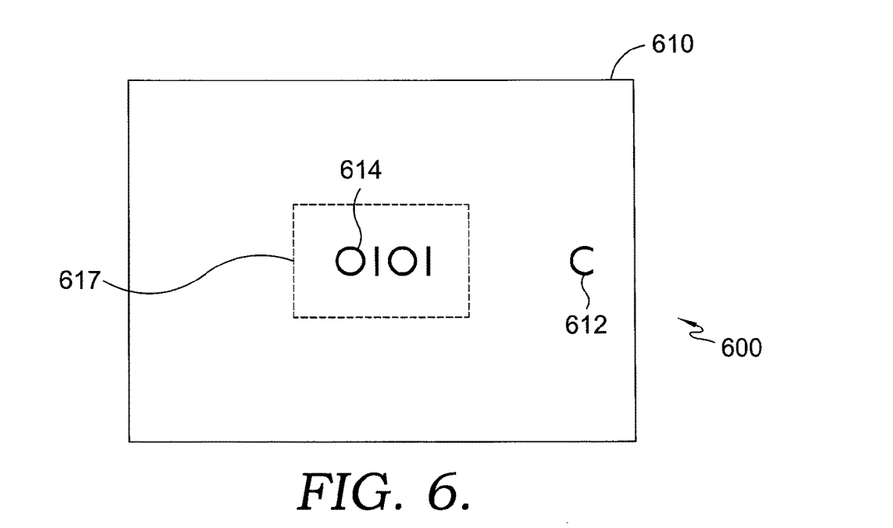
FIG. 6 illustrates the use of a display device to test differing fields of a test subject's vision.

Referring now to FIG. 6, a portion of a system 600 that tests different fields of vision of a subject (not illustrated) is shown. Display device 610 may comprise multiple regions. For example, a central region 617 may display an indicia 614 to test the central vision abilities of a subject. Meanwhile, another portion of display device 610 may test the peripheral vision abilities of a subject by displaying another indicia 612. A similar division of regions of display device 610 may test/train, for example, different quadrants of a subject's vision, a subject's visual abilities to the left or right, a subject's visual abilities up or down, or other discreet portions of a subject's field of vision. A system 600 testing/training a subject's visual/cognitive abilities in particular fields may be utilized in conjunction with any type of display device.

Figure 7:
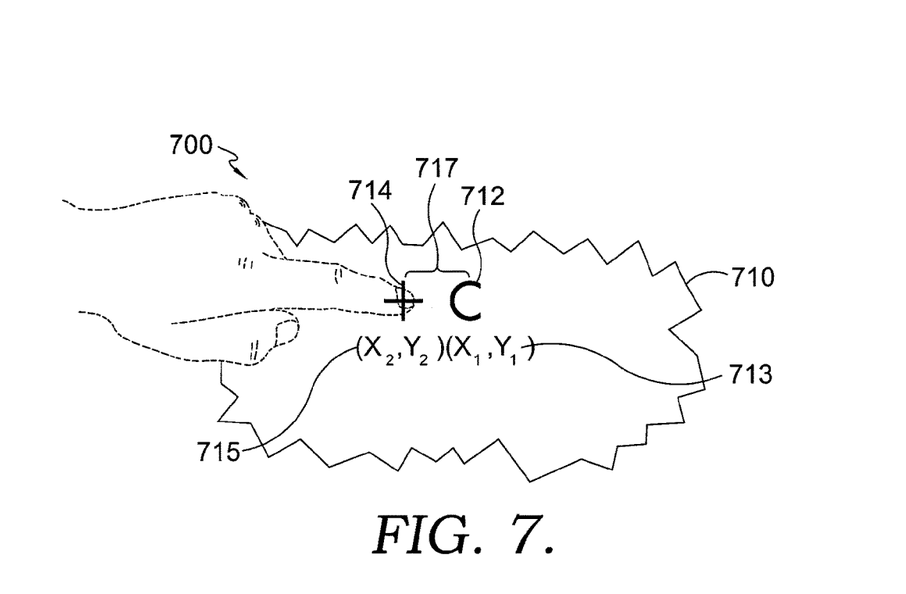
FIG. 7 illustrates a portion of a touch screen used to determine the accuracy of a subject's response.

Referring now to FIG. 7, a portion of a system 700 measuring the accuracy of a subject's eye-hand coordination response is illustrated. A portion of display device 710 may display thereon an indicia 712. Indicia 712 may have a first location 713 on display device 710, in this example denoted $x_1, y_1$. A response touch 714 from a subject, such as from finger 721, may be received at a second location 715, in this example denoted $x_2, y_2$. The distance 717 between a displayed indicia 712 and a touch response 714 may be determined using their respective locations on touch screen 710. It will be understood by one of skill in the art that, as both indicia 712 and touch response 714 consume a certain physical area of touch screen 710 that both the location of 713 of indicia 712 and the location 715 of touch response 714 may actually comprise a given area of display device 710 rather than a discreet point, and that distance calculations may make allowances for this.

Figure 8:
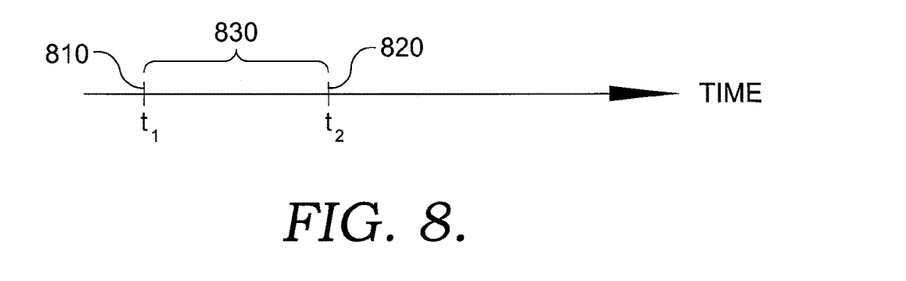
FIG. 8 illustrates the use of the present invention to measure the speed of a subject's response.

Referring now to FIG. 8, the measurement of the time elapsed between the display of an indicia and the receipt of a touch response is illustrated. As illustrated in FIG. 8, time progresses along the x-axis. An indicia may be displayed on a display device (not illustrated) at a first time 810 denoted $t_1$. A touch response may be received at a second time 820 denoted $t_2$. The elapsed time 830 between first time 810 and second time 820 may be used to measure the speed of response of a subject.

Figure 9:
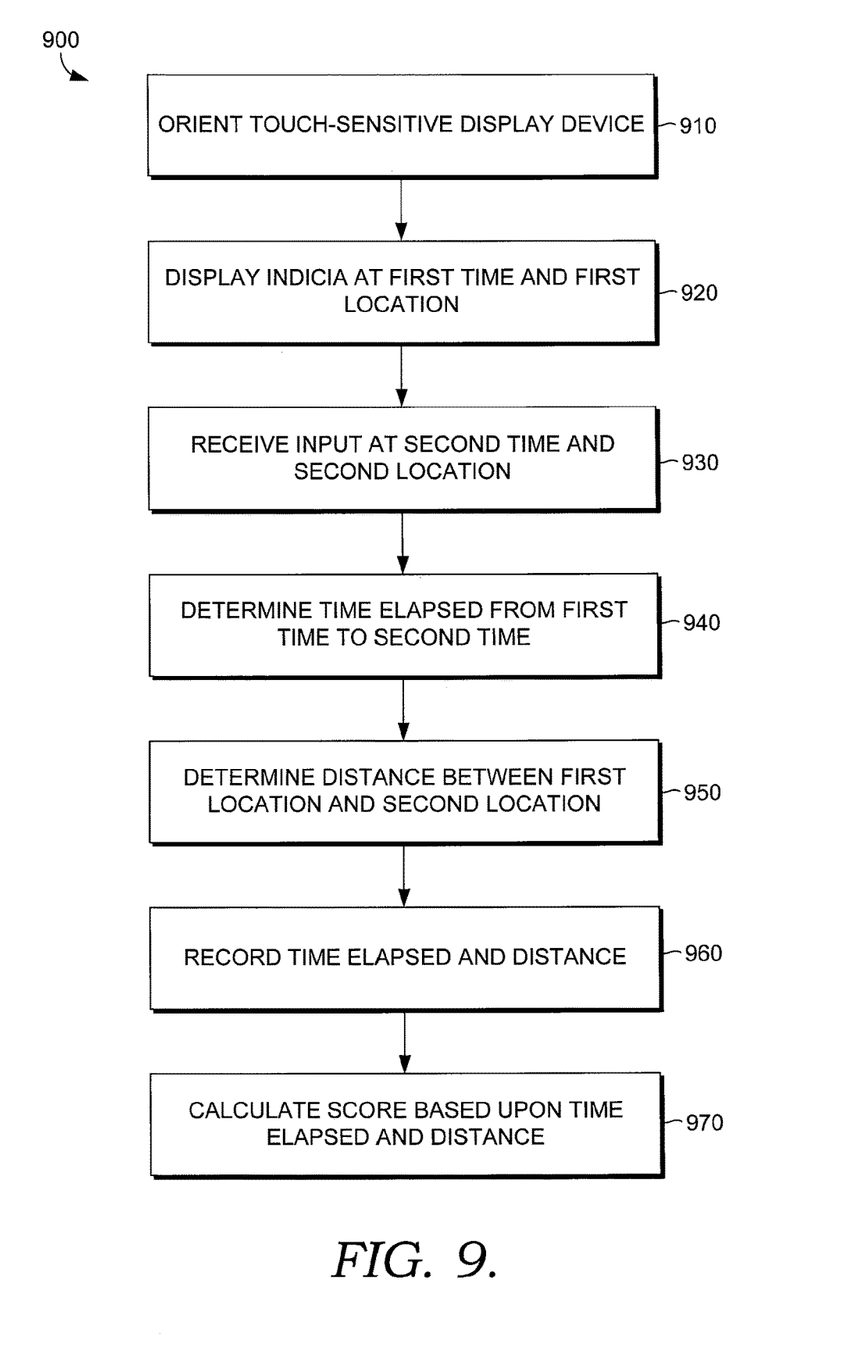
FIG. 9 illustrates a method in accordance with the present invention.

Referring now to FIG. 9, a method 900 in accordance with the present invention for utilizing a touch-sensitive display device to test a subject's eye-hand coordination is illustrated. In step 910 a touch-sensitive display device is oriented within reach of a subject. In step 920, an indicia is displayed on touch-sensitive display device beginning at a first time and occurring at a first location. In step 930 a touch input is received from a subject at a second time and at a second location on the touch-sensitive display device. In step 940 the time elapsed from the first time (at which the indicia was first displayed) to the second time (when the response was received) is determined. In step 950 the distance between the first location (where the indicia was displayed) and the second location (where the touch response was received) is determined. In step 960 the time elapsed between the first time and the second time and the distance between the first location and the second location are recorded, for example on a digital media in a test unit. In step 970 a score based upon the time elapsed and the distance is calculated. Step 970 of calculating a score may take into account a variety of information beyond simply the time elapsed and the distance, such as a subject's balance performance, head and/or eye movements, the different regions of a subject's field of view tested, biological/medical data or other criteria.

Figure 10:
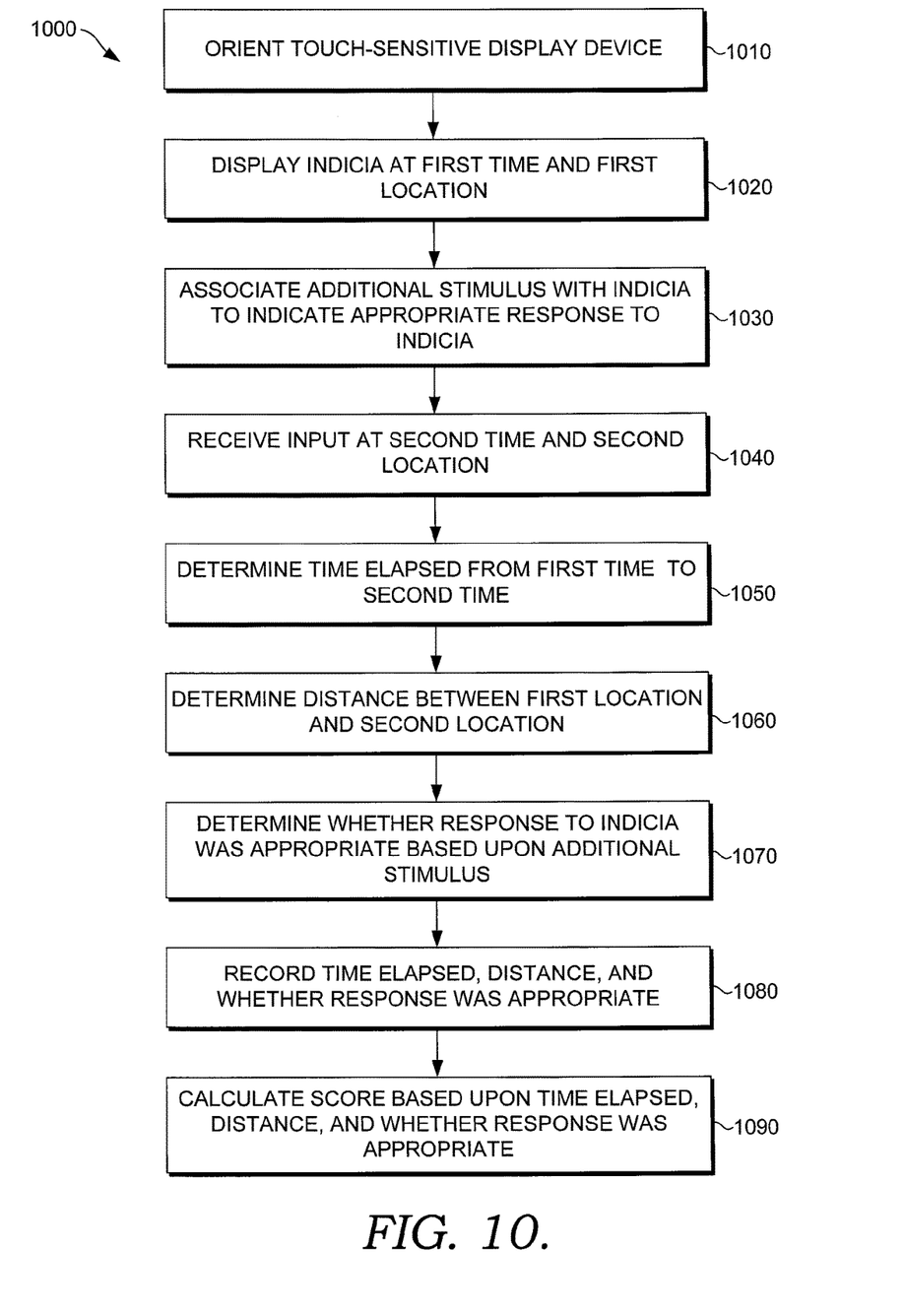
FIG. 10 illustrates a further method in accordance with the present invention.

Referring now to FIG. 10, a further method 1000 of testing a subject's eye-hand coordination and/or cognitive function is illustrated. In step 1010 a touch-sensitive display device is oriented within reach of a subject. In step 1020 a visual stimulus, such as an indicia, is displayed on the touch-sensitive display device beginning at a first time at a first location. In step 1030 a secondary stimulus is associated with the displayed visual stimulus to indicate an appropriate response to the indicia. Step 1030 may occur simultaneously with step 1020, may occur after step 1020, or may occur before step 1020. The association of a secondary stimulus with an indicia of step 1030 may comprise, for example, providing an indicia with a particular characteristic, such as orientation, color, type, shape, or value, that requires a response from a subject. There can be any number of possible secondary stimuli that could be associated with a visual stimulus in step 1030 and different possible stimuli could render different responses appropriate. For example, if a first possible secondary stimulus is provided the appropriate response might be to touch the displayed visual stimulus, but if a second possible secondary stimulus is provided the appropriate response might be to ignore the displayed visual stimulus. Possible secondary stimuli may be, for example, any sound, tactile sensations, traits of the displayed visual stimulus itself (such as its orientation, identification, color, visual pattern, flicker, movement on the display device, etc.), other displayed visual indicia, or any other indicia perceivable to a subject. At step 1040 an input is received. If the input received in step 1040 is a touch input, the touch input is received at a second time and at a second location. In step 1050 the time elapsed from the display of the visual stimulus, and/or from the association of the additional stimulus with the indicia, to the second time at which an input was received may be determined. In step 1060 the distance between the first location and the second location is determined. In step 1070 it is determined whether the response to the indicia and the associated additional stimulus was appropriate. For example, for an appropriate response might be to touch a displayed visual stimulus, to ignore a displayed visual stimulus, to verbally respond to a displayed visual stimulus (for example, by reciting identifying characteristics of the stimulus), or to provide a response using a motor input device. In step 1080 the time elapsed, the distance, and whether the response was appropriate is recorded on a digital media. In step 1090 a score may be calculated based upon the time elapsed, the distance, and whether the response was appropriate. One skilled in the art will appreciate that the score calculated in step 1090 may be based upon further information than merely than the time elapsed, distance, and appropriateness of a response, such as a subject's balance information, head and/or eye movement, biological/medical data or other information collected from the subject.

Figure 11:
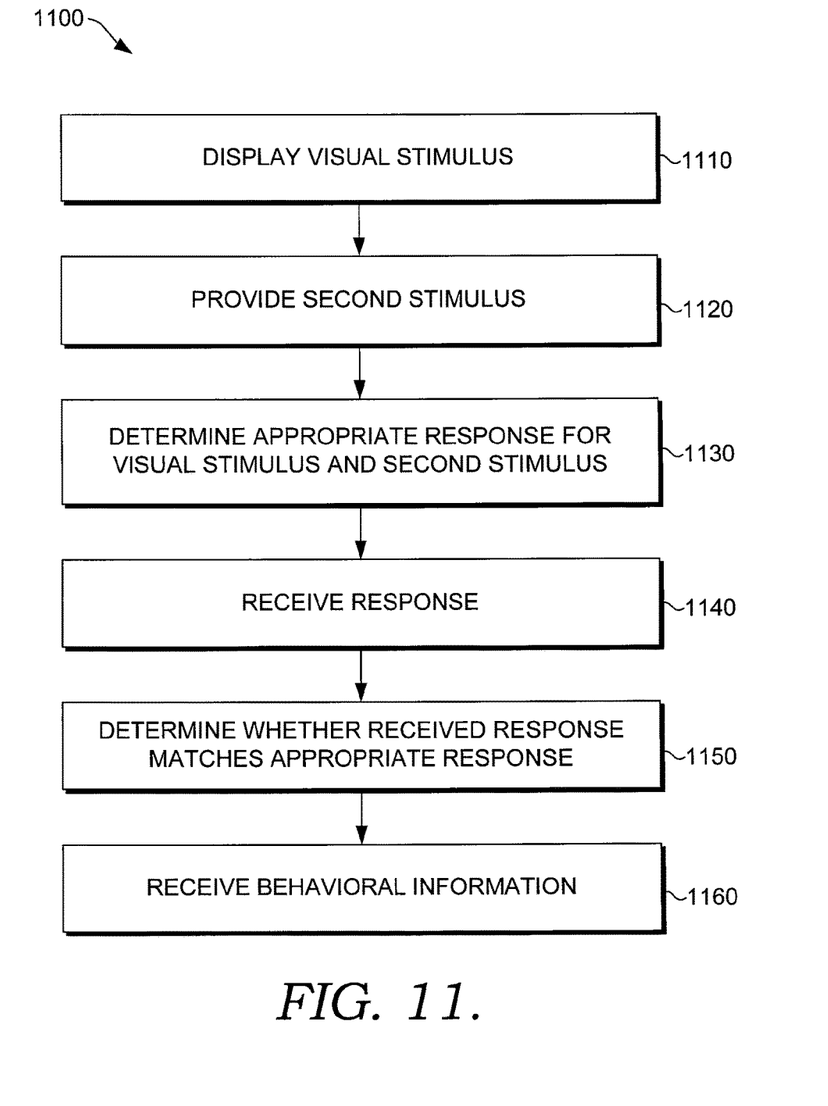
FIG. 11 illustrates a further method in accordance with the present invention.

Referring now to FIG. 11, a further method 1100 of testing/training a subject's visual and cognitive abilities is illustrated. In step 1110 a visual stimulus is displayed. Visual stimulus may be for example, a visual indicia. Step 1110 may insert a visual stimulus as part of the display of a video depicting an activity, whether animated, computer animated, recorded, or live action. For example, video depicting participation in a sport may be used and, optionally, indicia appropriate to the sport may be used. For example, a video depicting a pitcher releasing a ball toward home plate may be used and indicia indicating the type of pitch being thrown may be inserted on the ball, arm, and/or hand of the pitcher. In step 1120 a second stimulus is provided. The second stimulus provided in step 1120 may be an additional visual stimulus, such as a visual indicia, a sound, a tactile sensation, or any other type of stimulus. In step 1130 the appropriate response for the visual stimulus in combination with the second stimulus is determined. For example, if the visual stimulus is an indicia such as a Landolt C and the second stimulus is the orientation of the C, the appropriate response determined in step 1130 may be the movement of a joy stick on an input device in a direction corresponding to the orientation of the Landolt C. Other appropriate responses are near limitless, but may include, for example, the recitation of a string of displayed digits, touching a touch-sensitive display device, depressing a button or foot pedal, or any of a number of other responses. In step 1140 a response is received from a subject. It should be noted that the response received in step 1140 may or may not be the appropriate response. In step 1150 whether the response received matches the appropriate response is determined. In step 1160 behavioral information is received. Behavioral information may include a subject's balance ability and performance, head and eye movement, blood pressure, heart rate, amount of perspiration, or any other information.

The systems and methods described herein may be utilized to test and/or train a variety of visual, cognitive, and coordination skills. The types of display devices and other output devices used to provide stimuli to a subject are not limited to those described herein, but rather may utilize any type of device capable of providing stimuli to a subject. The systems and methods described herein are further not limited to any particular scoring algorithm or criteria, and the scoring algorithms and criteria may be adjusted for different subjects or as individual subjects progress in skill. Similarly, the number and types of stimuli provided to a subject and responses received by a subject are not limited to those described herein, and multiple types of stimuli and multiple types of responses may be provided and received in any individual testing/training session.

What is claimed is:

1. A method for testing and/or training with a testing unit that is communicatively coupled to a stability platform, a display device, a biological/medical monitor configured to be attached to a test subject to monitor biological/medical data of the test subject, and a first audio speaker, the method comprising:
    emitting a first sound from the first audio speaker;
    providing a visual image on the display device;
    determining an appropriate response to the first sound and the visual image by the test subject, the appropriate response indicated by the test subject through movement of the stability platform;
    receiving a response from the test subject at the stability platform in response to the first sound and the visual image;
    providing tactile feedback to the test subject with the stability platform based on the received response;
    measuring, using the biological/medical monitor, the biological/medical data of the test subject, wherein the biological/medical data is one or more of brain activity, blood pressure, heart rate, and perspiration of the test subject;
    determining whether the response received from the test subject is the appropriate response; and
    calculating and outputting a score based on at least the response received from the test subject and the biological/medical data.

2. The method of claim 1, wherein the stability platform is a balance board that can be tilted in a plurality of directions about a fulcrum point.

3. The method of claim 1, further comprising displaying at least one indicia on the display device and receiving at least one touch input on the display device from the test subject in response to the at least one indicia, the score further calculated and outputted based on the at least one touch input.

4. The method of claim 1, wherein the stability platform further comprises one or more sensors for detecting a shifting weight of the test subject.

5. The method of claim 1, further comprising a second audio speaker that emits noise when the response is received from the test subject.

6. The method of claim 1, wherein the display device is partially spherical.

7. The method of claim 6, wherein the partially spherical display device is configured to at least partially enclose the test subject.

8. The method of claim 6, wherein the partially spherical display device extends upward from a location horizontally aligned with the stability platform.

9. The method of claim 1, further comprising providing a wavelength filtering optical device configured to be worn by the test subject, wherein the visual image is provided based on the wavelength filtering optical device.

10. A system for testing and/or training of a test subject, the system comprising:
    a display device;
    a stability platform configured to receive directional input from the test subject and configured to provide tactile feedback to the test subject;
    a biological/medical monitor configured to be attached to the test subject to monitor biological/medical data of the test subject; and
    a test unit communicatively coupled to the display device, the stability platform, and the biological/medical monitor, the test unit configured for:
        outputting for display on the display device a visual stimulus;
        determining a directional orientation of the visual stimulus on the display device;
        receiving a directional input from the test subject at the stability platform indicating the directional orientation of the visual stimulus on the display device;
        based on the received directional input, providing tactile feedback to the test subject using the stability platform;
        receiving the biological/medical data of the test subject from the biological/medical monitor, wherein the biological/medical data is one or more of brain activity, blood pressure, heart rate, and perspiration of the test subject; and
        calculating and outputting a score for the test subject based on at least the determined directional orientation, the received directional input from the test subject, and the biological/medical data.

11. The system of claim 10, wherein the stability platform further comprises a balance board configured to tip about a fulcrum point, and wherein the score is further calculated and outputted based on a time elapsed between outputting the visual stimulus and receiving the directional input from the test subject.

12. The system of claim 10, further comprising at least one audio speaker communicatively coupled to the test unit and configured to emit a first sound.

13. The system claim 12, wherein the test unit is further configured to determine a direction of origin of the first sound and receive another directional input from the test subject at the stability platform indicating the direction of origin of the first sound, wherein the score is calculated and outputted additionally based on the other directional input received from the test subject.

14. The system of claim 10, wherein the biological/medical data is the brain activity of the test subject.

15. The system of claim 10, wherein the biological/medical data is the heart rate of the test subject.

16. The system of claim 10, wherein the biological/medical data is the perspiration of the test subject.

17. A method for testing and/or training coordination with a testing unit that is communicatively coupled to a stability platform, a partially spherical display device, a biological/medical monitor configured to be attached to a test subject to monitor biological/medical data of the test subject, and a first audio speaker, the method comprising:
    emitting a first sound from the first audio speaker, the test unit configured to determine a direction of origin of the first sound and an appropriate response to the first sound by the test subject based on the direction of origin of the first sound;
    receiving an input from the test subject indicating a direction of origin of the first sound;
    providing tactile feedback to the test subject with the stability platform based on the received input;
    determining a time elapsed between the first sound being emitted and the input being received;
    measuring, using the biological/medical monitor, the biological/medical data of the test subject, wherein the biological/medical data measured is one or more of brain activity, blood pressure, heart rate, and perspiration of the test subject; and
    calculating a score based on the time elapsed, the biological/medical data, and the input indicating the direction of origin.

18. The method of claim 17, wherein the stability platform comprises a balance board upon which the test subject stands.

19. The method of claim 17, further comprising altering the difficulty of the testing and/or training based on the score.

20. The method of claim 17, wherein the partially spherical display device is touch sensitive and the input is received at the partially spherical display device.

* * * * *

UNITED STATES PATENT AND TRADEMARK OFFICE
CERTIFICATE OF CORRECTION

| | |
|---|---|
| PATENT NO. | : 10,226,171 B2 |
| APPLICATION NO. | : 12/595210 |
| DATED | : March 12, 2019 |
| INVENTOR(S) | : Alan W. Reichow et al. |

Page 1 of 1

It is certified that error appears in the above-identified patent and that said Letters Patent is hereby corrected as shown below:

In the Claims

Column 10, Line 04: In Claim 13, after "system" insert -- of --.

Signed and Sealed this
Seventh Day of May, 2019

Andrei Iancu
*Director of the United States Patent and Trademark Office*